(12) United States Patent
Dukan et al.

(10) Patent No.: US 11,199,542 B2
(45) Date of Patent: Dec. 14, 2021

(54) METHOD FOR LABELING SPECIFICALLY LIVING BACTERIA COMPRISING THE USE OF MODIFIED NON ENDOGENOUS MONOSACCHARIDE COMPOUNDS

(71) Applicants: CENTRE NATIONAL DE LA RECHERCHE SCIENTIFIQUE (CNRS), Paris (FR); UNIVERSITE D'AIX-MARSEILLE, Marseilles (FR)

(72) Inventors: Sam Dukan, Marseilles (FR); Boris Vauzeilles, Sceaux (FR); Jordi Mas Pons, Rubi (ES); Aurélie Baron, L'isle Adam (FR)

(73) Assignees: CENTRE NATIONAL DE LA RECHERCHE SCIENTIFIQUE (CNRS), Paris (FR); UNIVERSITE D'AIX-MARSEILLE, Marseilles (FR)

( * ) Notice: Subject to any disclaimer, the term of this patent is extended or adjusted under 35 U.S.C. 154(b) by 370 days.

(21) Appl. No.: 15/570,416

(22) PCT Filed: May 3, 2016

(86) PCT No.: PCT/EP2016/059880
§ 371 (c)(1),
(2) Date: Oct. 30, 2017

(87) PCT Pub. No.: WO2016/177724
PCT Pub. Date: Nov. 10, 2016

(65) Prior Publication Data
US 2018/0143193 A1 May 24, 2018

(30) Foreign Application Priority Data
May 4, 2015 (EP) ..................................... 15166250

(51) Int. Cl.
| | |
|---|---|
| *G01N 33/569* | (2006.01) |
| *G01N 33/58* | (2006.01) |
| *C12Q 1/02* | (2006.01) |
| *C12Q 1/04* | (2006.01) |

(52) U.S. Cl.
CPC ......... *G01N 33/56911* (2013.01); *C12Q 1/02* (2013.01); *C12Q 1/04* (2013.01); *G01N 33/582* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 9,057,093 B2 * | 6/2015 | Fovet | ..................... | C12Q 1/04 |
| 9,181,204 B2 * | 11/2015 | Leibl | ..................... | C07D 249/06 |
| 9,181,575 B2 * | 11/2015 | Fovet | ..................... | C12Q 1/06 |
| 9,492,473 B2 * | 11/2016 | von Maltzahn | ...... | A61K 31/715 |
| 9,493,809 B2 * | 11/2016 | Dukan | ..................... | C12Q 1/04 |
| 10,082,509 B2 * | 9/2018 | Dukan | ..................... | G01N 33/58 |
| 2014/0363817 A1 * | 12/2014 | Dukan | ..................... | C12Q 1/04 |
| | | | | 435/6.11 |
| 2015/0143200 A1 * | 5/2015 | Chinnakkonda Vidyapoornachary | ..................... | G06F 1/3275 |
| | | | | 714/770 |

(Continued)

FOREIGN PATENT DOCUMENTS

| | | | | |
|---|---|---|---|---|
| EP | 2 617 833 | | 7/2013 | |
| EP | 2617833 A1 * | | 7/2013 | ............... C12Q 1/04 |

(Continued)

OTHER PUBLICATIONS

International Search Report for PCT/EP2016/059880, dated Jun. 24, 2016, 5 pages.

(Continued)

*Primary Examiner* — Nita M. Minnifield
(74) *Attorney, Agent, or Firm* — Nixon & Vanderhye, P.C.

(57) ABSTRACT

The invention relates to a method for labeling specifically living bacteria, comprising the steps of: a) incubating said bacteria of said sample with at least one modified monosaccharide compound comprising a first reactive chemical group capable to chemically react with a second reactive group, so that a residue bearing said first reactive group is incorporated into the envelope of such bacteria, and b) contacting said modified monosaccharide residue incorporated within the envelope of the bacteria with a labeling molecule comprising a said second reactive group, for generating the chemical reaction of said first reactive group with said second reactive group, characterized in that said modified monosaccharide compound has the following formula (I), or a salt thereof: Wherein —A, B and C can be independently H, OH, $NH_2$, OH and $NH_2$ being substituted or not by protecting groups thereof and —D is an alkyl chain in $C_2$ to $C_4$, each carbon being substituted or not by OH or $NH_2$, OH and $NH_2$ being substituted or not by protecting groups thereof and —at least one of A, B, C or D groups is substituted by a said first reactive group.

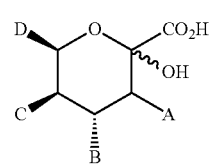

(I)

20 Claims, No Drawings

(56) References Cited

U.S. PATENT DOCUMENTS

| | | | | |
|---|---|---|---|---|
| 2016/0238609 A1* | 8/2016 | Dukan | ............ | C12Q 1/02 |
| 2017/0030908 A1* | 2/2017 | Dukan | ............ | C12Q 1/04 |
| 2018/0143193 A1* | 5/2018 | Dukan | ............ | C12Q 1/02 |
| 2018/0143200 A1* | 5/2018 | Dukan | ............ | C12Q 1/02 |

FOREIGN PATENT DOCUMENTS

| | | | | |
|---|---|---|---|---|
| WO | WO 2013/107759 | 7/2013 | | |
| WO | WO-2013107759 A1 * | 7/2013 | ............ | C12Q 1/04 |
| WO | WO-2015063173 A1 * | 5/2015 | ............ | C12Q 1/02 |

OTHER PUBLICATIONS

Written Opinion of the ISA for PCT/EP2016/059880, dated Jun. 24, 2016, 7 pages.

Chung et al., "Dioxygenases in Burkholderia ambifaria and Yersinia pestis that hydroxylate the outer Kdo unit of lipopolysaccharide", Proceedings of the National Academy of Sciences, vol. 108, No. 2, Jan. 11, 2011, pp. 510-515.

Jaipuri et al., "Synthesis and Quantitative Evaluation ofGlycero-D-manno-heptose Binding to Concanavalin A by Fluorous-Tag Assistance", Angewandte Chemie International Edition, vol. 47, No. 9, Jan. 18, 2008, pp. 1707-1710.

Sherratt et al., "Copper-catalysed cycloaddition reactions of nitrones and alkynes for bioorthogonal labelling of living cells", RSC Adv, vol. 4, No. 87, Jan. 1, 2014, pp. 46966-46969.

\* cited by examiner

METHOD FOR LABELING SPECIFICALLY LIVING BACTERIA COMPRISING THE USE OF MODIFIED NON ENDOGENOUS MONOSACCHARIDE COMPOUNDS

This application is the U.S. national phase of International Application No. PCT/EP2016/059880 filed 3 May 2016, which designated the U.S. and claims priority to EP Patent Application No. 15166250.9 filed 4 May 2015, the entire contents of each of which are hereby incorporated by reference.

The present invention concerns a method for labeling of living bacteria, in incorporating compounds hearing a reactive group into the envelope of said bacteria. The present invention provides more particularly a method allowing labeling of bacteria The term ««"envelope»»" herein includes any wall, layer or membrane at the surface of the bacterium, especially the cellular wall including, the envelope more particularly the inner plasma membrane and the peptidoglycan layer for the bacteria as well as the outer membrane for Gram negative bacteria.

The present invention concerns a method for labeling of living bacteria in incorporating modified monosaccharide compounds into the envelope of said bacteria, more particularly in the polysaccharides (especially LPS or CPS) of the envelope of bacteria. The present invention provides more particularly a method allowing labeling of both Gram negative and Gram positive bacteria using a modified non endogenous monosaccharide, namely which is not specifically present within the envelope of the thus labeled bacterium.

WO 2013/107759 discloses a method of labeling living bacteria, more particularly, Gram negative bacteria. The method essentially consists in incorporating in the membrane of said bacteria by assimilation an analog of endogenous monosaccharide compound of the ulosonic acid type modified so that it bears a so-called first reactive chemical function such as azide (—$N_3$) or alkyne (—C≡CH) group thus enabling a reaction of this first reactive group with a molecule bearing the complementary reactive group especially through a so-called click chemistry reaction.

More particularly, it has been disclosed in WO 2013/107759 that such modified analogs of endogenous sugars comprising ulosonic acid or ulosonate residue are particularly advantageous in that such residues can be found in glycans of the bacterial membrane, especially LPS of all of the Gram negative bacteria, and moreover they can be directly assimilated in the same form into which they will be incorporated in the said glycans of the LPS of Gram negative bacteria.

Ulosonic acids (also called ketoaldonic acids, or aldulosonic acids) are monosaccharides of the ketose family, presenting a ketone function at C-2, and a carboxylic acid at C-1. Octulosonic and nonulosonic acids are found in diverse natural glycans, including different forms of bacterial glycans (especially LPS, capsular polysaccharide, glycoproteins). The biosynthetic pathway leading to the elaboration of these glycans generally involves the free ulosonic acid as an intermediate, which is then directly activated in the form of a CMP-sugar donor. All of the Gram negative bacteria LPS comprise said ulosonate residues.

More accurately, the method disclosed in WO 2013/107759 is a method for specifically labeling living bacteria of a given category of bacteria in a sample comprising bacteria, the method comprising the steps of:

a) incubating said bacteria of said sample with at least one analog of a monosaccharide compound, said monosaccharide being an endogenous monosaccharide residue of glycans of the outer membrane of such given category of bacteria, the said endogenous monosaccharide residue comprising an ulosonic acid or ulosonate salt residue, the said analog of a monosaccharide compound being a modified monosaccharide substituted at a given position by a first reactive chemical group capable to react with a second reactive group of a labeling molecule, and b) contacting said bacteria with a said labeling molecule comprising a said second reactive group, for generating the reaction of said first reactive group of said analog residue incorporated within said glycans of the outer membrane of said living bacteria with said second reactive group of said labeling molecule.

Particularly, in WO 2013/107759 the said analog of monosaccharide is a substituted ulosonic acid having one of the following formula (I') or an ulosonate salt thereof:

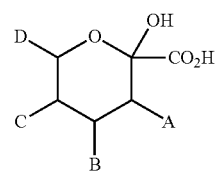

I'

A, B and C can be independently H, OH, $NH_2$, OH and $NH_2$ being substituted or not by protecting groups thereof, and D is an alkyl chain in $C_2$ to $C_4$, and at least one of A, B, C or D groups is substituted by a said first reactive group.

In WO 2013/107759, the said analog of monosaccharide incubated with the living bacteria in step a) and then incorporated within its outer membrane after assimilation by the bacteria, can be identical to the endogenous monosaccharide incorporated in the glycans chain of the outer membrane except it is modified only by substitution of the said first reactive group.

The goal of the present invention was to find out other monosaccharidic compounds capable to be assimilated within other bacteria or a broader range of bacteria and especially within both Gram negative and Gram positive bacteria and presenting advantageous and different properties as to their specificity of incorporation in respect to the concerned category of bacteria.

More accurately, the present invention provides a method for labeling specifically living bacteria in a sample comprising bacteria, the method comprising the steps of:

a) incubating said bacteria of said sample with at least one modified monosaccharide compound comprising a first reactive chemical group capable to chemically react with a second reactive group, so that a residue bearing said first reactive group, preferably a monosaccharide residue, is incorporated into the envelope of said living bacteria, especially into the polysaccharides of the envelope of said bacteria, more especially into the LPS or CPS of the outer membrane of said bacteria, and b) contacting said residue incorporated into the envelope of said living bacteria, with a labeling molecule comprising a said second reactive group, for generating the chemical reaction of said first reactive group of said residue incorporated within said living bacteria with said second reactive group of said labeling molecule, resulting in a covalent link, characterized in that the said residue is not an endogenous ulosonic acid residue of the envelope of said bacteria, preferably said residue is a not naturally occurring stereoisomer of an endogenous ulosonic acid residue of the envelope of said bacteria, especially not naturally occurring stereoisomer of an endogenous ulosonic acid residue of the polysaccharides of the outer membrane of said bacteria, said modified monosaccharide compound having the following formula (I), or a salt thereof:

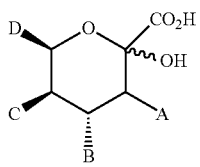

Wherein
A, B and C can be independently H, OH, $NH_2$, OH and $NH_2$ being substituted or not by protecting groups thereof, preferably OH and $NH_2$ being substituted by alkyl, hydroxyalkyl, acyl, formyl or imidoyl groups, and D is an alkyl chain in $C_2$ to $C_4$, each carbon being substituted or not by OH or $NH_2$, OH and $NH_2$ being substituted or not by protecting groups thereof, preferably OH and $NH_2$ being substituted by alkyl, hydroxyalkyl, acyl, formyl or imidoyl groups, and at least one of A, B, C or D groups is substituted by a said first reactive group.

More particularly, such compound of formula (1) is a substituted ulosonic acid or an ulosonate salt thereof.

The expression "not naturally occurring" means that the said monosaccharide compound which is modified by the said first reactive group, namely the unmodified monosaccharide residue of the said modified monosaccharide compound is neither recovered as an endogenous monosaccharide residue of the glycans of the envelope of said bacteria nor recovered as a precursor thereof in the biosynthetic pathway of such endogenous monosaccharide residue of the glycans of the envelope of said bacteria.

The bacteria comprise Gram positive bacteria and Gram negative bacteria as well as bacteria which are neither Gram negative nor Gram positive.

Such compound of formula (I) can be assimilated by a broad range of category of bacteria.

According to the present invention, the accurate mechanisms by which said modified monosaccharide compound is assimilated by the bacteria in incorporating a said residue bearing said first reactive group therein is not quite determined.

However, it appears that said monosaccharide compound is different than endogenous monosaccharides residues of the envelope of said bacteria and more particularly, in the case of Gram negative bacteria different than endogenous monosaccharides residues of polysaccharides of the outer membrane of such bacteria, such as LPS or capsular polysaccharide (CPS) of bacteria, and then being nevertheless capable to penetrate and be incorporated into said bacteria.

The expression "endogenous monosaccharide residue" means a residue, naturally present in the envelope of said bacteria, more particularly in polysaccharides of the envelope of said bacteria.

More particularly, in the method of the present invention, said modified monosaccharide compounds are not naturally occurring stereoisomers of modified endogenous monosaccharides of the above formula (I') disclosed and claimed in WO 2013/107759. The compounds of the present invention might be metabolized and converted during the incubation step a) so as to become incorporated within glycans of the envelop of said bacteria, likely converted into modified endogenous monosaccharides residues of the glycans of the envelop of such bacteria, namely endogenous monosaccharides residues modified in that they bear the said first reactive groups.

Alternatively, it might be that said modified monosaccharide compounds can be metabolized, converted or degraded in a molecule giving rise to said residue other than monosaccharide residue incorporated into said bacteria or giving rise to a precursor of said residue.

The formula with a pyranosic cycle (I) can be in part in equilibrium with a following furanosic cycle (II) although generally the formula (I) is predominant:

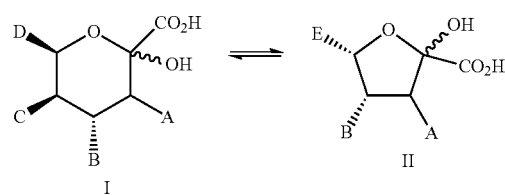

with C=OH, and E being such that E=CHOHD.

More particularly, for OH the protecting group can be preferably an alkyl, hydroxyalkyl, acyl or formyl group.

More particularly, for $NH_2$ the protecting groups can be selected among alkyl, hydroxyalkyl, acyl, formyl or imidoyl groups.

$NH_2$ can be protected by one or two protecting groups, especially one $CH_3$ group and one alkyl, hydroxyalkyl, acyl, formyl or imidoyl group, especially acetyl (Ac), acetimidoyl (Am), N-methyl-acetimidoyl, N,N-dimethyl-acetimidoyl, formyl (Fo), or hydroxybutanoyl group.

It must be understood that the said monosaccharide residue of said modified monosaccharide compound are not naturally occurring stereoisomers of endogenous monosaccharide residue of compounds of formula (I') of the envelope in the said Bacteria:

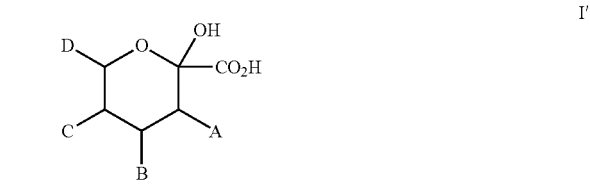

Especially the following stereoisomer as in Kdo:

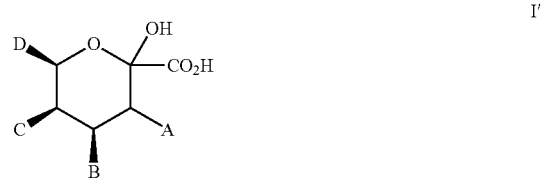

Preferably, said modified monosaccharide compound is a compound having the said formula (I), or a salt thereof:

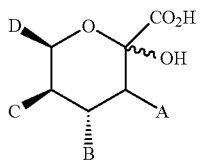

Wherein:
A is H, OH, $NH_2$, OH and $NH_2$ being substituted or not by said protecting group, and
B is H, OH, $NH_2$, OH and $NH_2$ being substituted or not by said protecting group, and
C is H, OH, $NH_2$, OH and $NH_2$ being substituted or not by said protecting group, and
D is a $C_2$ or $C_4$ alkyl, each carbon being substituted or not by OH or $NH_2$, OH and $NH_2$ being substituted or not by protecting groups thereof, preferably OH and $NH_2$ being substituted by alkyl, hydroxyalkyl, acyl, formyl or imidoyl groups, and
at least D group is substituted by a said first reactive group Ra.

More particularly, the said modified monosaccharide is a compound of formula (I) wherein D=-CHOH—$CH_2$—OH, A=H, B=OH, C=OH, OH of B, C and D being substituted or not by a protecting group preferably an alkyl, hydroxyalkyl, acyl or formyl group, and at least one OH of B, C or D groups being substituted by a said first reactive group Ra.

Preferably, the said modified monosaccharide compound is a compound (I) substituted wherein D=-CHOH—$CH_2$—Ra, A=H, B=OH, C=OH, OH of B. C and D being substituted or not by preferably an alkyl, hydroxyalkyl, acyl or formyl group.

More preferably, the said monosaccharide compound is a compound having the following stereoisomer formula (Ia), or a salt thereof wherein:

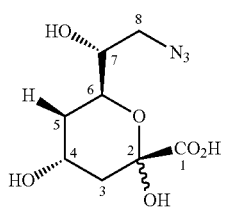

(Ia) is the C-4 epimer of 8-azido-3,8-dideoxy-D-manno-octulosonate named 8-azido-3,8-dideoxy-D-gluco-octulosonate and can be also represented as:

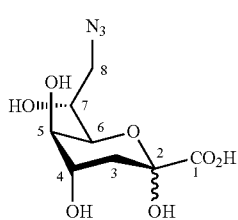

Said compound (Ia) is a modified 4eKdo (Ia') which is a not naturally occurring epimer at position C-4 of the endogenous ulosonic acid Kdo (I-1'):

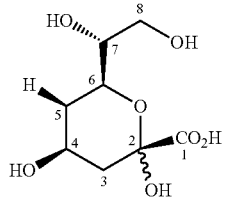

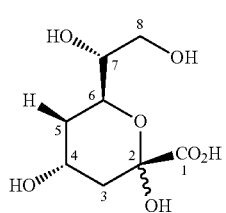

As per the conventional representation of formula, the carbon atoms in the positions C-1 to C-n of the various above cycles and substituents H bound to these carbon atoms are not represented.

The said chemical reaction between said first and second reactive groups results in a covalent link which in few examples can be a covalent coordination link in a metallic complex coordinated with ligands.

Preferably, the said first reactive group Ra is selected among groups consisting in or bearing the group azido (—$N_3$) and groups consisting in or bearing the group alkyne (—C≡C—), the said first reactive group being preferably the group azido, and the said second reactive group is selected among groups consisting in or bearing respectively the groups alkyne and azido, the said second reactive group being preferably the group alkyne, and reacting the said azido reactive group with the said alkyne reactive group is carried out in performing an azide alkyne cycloaddition.

More preferably, Ra is —$N_3$ or —C≡CH, preferably —$N_3$.

Such compound of formula (I) can be assimilated by a broad range of category of bacteria and giving rise to incorporating a said residue into the envelope of such bacteria.

More particularly, the compound of formula (I) can be used for labeling Bacteria which can be selected among interalia in the following genus of bacteria: *Bacillus, Enterococcus, Escherichia, Klebsiella, Legionella, Listeria, Micrococcus, Neisseria, Proteus, Providencia, Pseudomonas, Salmonella, Serratia, Staphylococcus, Stenotrophomonas, Streptococcus, Vibrio*.

More particularly, the compound of formula (I) can be used for labeling Gram negative as well as Gram positive bacteria which can be selected among interalia in the following genus of bacteria:

More particularly, among the Gram negative bacteria which can assimilate compounds of formula (I), preferably said compound of formula (Ia), the following species can be cited: *Escherichia coli, Klebsiella pneumoniae, Legionella pneumophila, Neisseria gonorrhoeae, Neisseria meningitidis, Proteus mirabilis, Providencia stuartii, Pseudomonas fluorescens, Salmonella typhimurium, Serratia marcescens, Stenotrophomonas mahlophilia, Vibrio cholera*.

More particularly, among the Gram positive bacteria which can assimilate compounds of formula (I), preferably, said compound of formula (Ia), the following species can be cited: *Bacillus cereus, Enterococcus durans, Enterococcus faecalis, Listeria monocytogenes. Micrococcus luteus, Staphylococcus aureus, Staphylococcus aureus aureus, Staphylococcus epidermis, Staphylococcus saprophyticus, Streptococcus agalactiae.*

Among the above bacteria, the following ones did not assimilate Kdo-$N_3$ (I-1') of WO 2013/107759: *Neisseria gonorrhoeae, Enterococcus faecalis, Listeria monocytogenes, Micrococcus luteus, Staphylococcus aureus, Staphylococcus aureus aureus, Staphylococcus epidermis* all of them being Gram positive bacteria except *Neisseria gonorrhoeae*.

More particularly, the incubation time at step a) is from 1 hr to 24 hr, preferably from 1 hr to 12 hr and the modified monosaccharide compound concentration is from $10^{-5}$ M to 1 M, for detecting a bacteria concentration preferably of no more than $10^{11}$ cell/ml, more particularly no more than $10^9$ cell/mi.

Living bacteria are bacteria capable of multiplying. As most of the sanitary regulations refer to the numbering of bacteria capable to multiply, especially capable to multiply on a solid growth medium, advantageously, the present invention provides more particularly a method for labeling specifically bacteria capable of multiplying wherein said bacteria are incubated in a culture medium in (liquid medium) or on (solid medium) which said bacteria are capable to multiply.

Severe pathogens are hiding amongst above mentioned bacteria, and the rapid labelling and/or detection of living bacteria represents a major sanitary challenge. The modified monosaccharides of the present invention are rapidly assimilated by the bacteria and enable fast labeling and detection thereof the overall process taking less than one day, of living wild type bacteria. This method is very rapid in comparison to usual detection of living bacteria which needs normally between 2 days and more than one month depending on the bacterial strain.

Advantageously, the present invention comprises the further step (c) of detecting living bacteria in detecting whether said bacteria comprise said labeling molecule bound to their envelope and/or immobilizing said living bacteria bearing said labeling molecule onto a solid substrate, wherein said labeling molecule is a molecule comprising a detectable substance or capable to react or to be bound to a detectable substance or said labeling molecule is a first molecule bearing a said second reactive group, said first molecule being capable to react or to be bound to a second molecule and/or to a solid substrate, preferably said second molecule comprising a detectable substance and/or said second molecule being bound or capable to be bound to a said solid substrate.

Accordingly, the present invention enables (a) numbering or identification of detected living bacteria as well a (b) concentrating and/or isolating living bacteria immobilized on a solid support; especially with a solid support constituted of magnetic beads bearing the said second reactive group.

More particularly, said labeling molecule is a detectable molecule comprising a detectable substance, the method comprising the step c) of detecting living bacteria in detecting whether said bacteria comprise said detectable molecule bound to the glycans of their outer membrane.

The said detecting step c) can be carried out in a liquid medium or on a solid substrate.

More particularly, said labeling molecule can be a detectable molecule, namely a molecule consisting in or bearing a detectable substance, namely a substance capable to be detected by techniques know by one skilled in the art, such as fluorescence, colorimetry or luminescence.

More particularly, said labeling molecule is a first ligand or first binding protein bearing a said second reactive group and in step c) said living bacteria coupled to said first ligand or first binding protein is detected and/or immobilized by contacting said first ligand or first binding protein with a second ligand or second binding protein reacting or binding specifically to said first ligand or first binding protein.

More particularly, said labeling molecule is a first ligand, preferably biotin, bearing a said second reactive group, and in step c) said living bacteria coupled to said first ligand are detected by reaction of said bacteria with an antibody or another protein specific to said first ligand, said antibody bearing a detectable substance, preferably a fluorochrome or luminescent molecule or an enzyme.

The present invention provides also a kit for carrying out the method of the present invention comprising:
- a said modified monosaccharide compound of formula (I) and
- a said labeling molecule comprising a said second reactive group capable of reacting with said first reactive group, and
- if required, reactants for generating the reaction of said first reactive group with said second reactive group of said labeling molecule, and
- preferably, a culture or incubation medium allowing the growth of a said bacteria, preferably specific to the growth of said bacteria.

Preferably, the said first reactive group Ra is selected among groups consisting in or bearing the group azido (—$N_3$) and groups consisting in or bearing the group alkyne (—C≡C—), and the said second reactive group Rb is selected among groups consisting in or bearing respectively the groups alkyne (—C≡C—) and azido (—$N_3$), and reacting the said azido reactive group with a said alkyne group (—C≡C—) is carried out in performing an azide alkyne cycloaddition.

An azide alkyne cycloaddition is a well-known so-called click chemistry reaction in the presence or not of a copper catalyst wherein the azide group reacts with the alkyne group to afford a triazole. More particularly, the reaction can be carried out in copper catalyzed conditions in the presence of a tris-triazolyl ligand, preferably TGTA. More particularly, the detectable molecule is a fluorochrome bearing a terminal alkyne group.

More particularly, the reaction can be carried out in the presence of a tris-triazole ligand such as TGTA (Tris((1-(β-D-glucopyranosyl)-1H-[1,2,3]-triazol-4-yl)methyl)amine) or TBTA (Tris-[(1-benzyl-1H-1,2,3-triazol-4-yl)methyl] amine) and an Alexa labeling molecule bearing a terminal alkyne group with a catalyst so as to perform an azide alkyne cycloaddition of the said fluorochrome and said analog compound of formula (I).

Other appropriate ligands frequently used are: tris(3-hydroxypropyltriazolylmethyl)amine (THPTA), 2-(4-((bis((1-tert-butyl-1H-1,2,3-triazol-4-yl)methyl)amino)methyl)-1H-1,2,3-triazol-1-yl)ethanesulfonic acid (BTTES), tris ((1-((O-ethyl) carboxymethyl)-(1,2,3-triazol-4-yl))methyl) amine, bathophenanthroline disulfonate, or Tris(2-benzimidazolylmethyl)amines.

Alternatively, azide alkyne cycloaddition can be performed in the absence of copper, if a strained alkyne is used, such as azadibenzocyclooctyne (ADIBO, DIBAC or DBCO) or tetramethoxydibenzocyclooctyne (TMDIBO).

Other appropriate strained alkynes frequently used for copper-free reaction include: cyclooctyne (OCT), aryl-less cyclooctyne (ALO), monofluorocyclooctyne (MOFO), difluorocyclooctyne (DIFO), dibenzocyclooctyne (DIBO), dimethoxyazacyclooctyne (DIMAC), biarylazacyclooctynone (BARAC), bicyclononyne (BCN), tetramethylthiepinium (TMTI, TMTH), difluorobenzocyclooctyne (DIFBO), oxa-dibenzocyclooctyne (ODIBO), carboxymethylmonobenzocyclooctyne (COMBO), or benzocyclononyne.

Other reactive groups and other reactions are possible such as; Staudinger Ligation (first reactive group=azide and second reactive group=phosphine), copper-free click-chemistry (first reactive group=azide and second reactive group=constrained alkyne (intracyclic alkyne)), carbonyl condensation (first reactive group=aldehyde or ketone and second reactive group=hydrazide or oxyamine), thiol-ene click chemistry (first reactive group=thiol and second reactive group=alkene), nitrile-oxide-ene click chemistry (first reactive group=nitrile oxide or aldehyde, oxime, or hydroxymoyl chloride or chlororoxime and second reactive group=alkene or alkyne), nitrile imine-ene click chemistry (first reactive group=nitrile imine or aldehyde, hydrazone, or hydrazonoyl chloride or chlorohydrazone and second reactive group=alkene or alkyne), inverse electron demand Diels-Alder ligation (first reactive group=alkene and second reactive group=tetrazine), isonitrile-tetrazine click chemistry (first reactive group=isonitrile and second reactive group=tetrazine), Suzuki-Miyaura coupling (first reactive group=aryl halide and second reactive group=aryl boronate), His-tag (first reactive group=oligo-histidine and second reactive group=nickel-complex or nickel ligand).

In the above-mentioned listing of groups involved in the reactions, the first reactive group and the second reactive group can be permuted. All the above mentioned chemical reactions result in a covalent link.

Other and higher specificity of detection can be obtained in incubating the bacteria sample with two said different modified monosaccharide compounds and two different detectable molecules.

In another particular embodiment of the method of the present invention, the said incubation of step a) and reaction of step b) are carried out on a membrane filter so that the cultivated bacteria emanating from a same original bacterium which has been multiplied are grouped together and can be visualized with a microscope and the said detectable molecule can be detected by visualization with a said microscope. Therefore, the number of cultivable bacteria can be quantified thereby.

This embodiment enables to filter the tested sample on said membrane filter such as a polyester membrane, prior to assimilation of the said modified monosaccharide to avoid over-estimation of living bacteria due to possible growth during the assimilation period. Indeed, when cells fixed on the top of such membrane start to grow, they stay together and form a micro-colony that can be easily detected as coming from the same single cell. Therefore, this enables to number by counting the cultivable bacteria.

The present invention also provides a kit for carrying out the method of the invention further comprising a culture or incubation medium allowing the growth of a said bacteria, preferably specific to the growth of said bacteria.

Preferably, the said culture or incubation medium further comprises agents enhancing and/or accelerating the growth speed and/or the capacity to form colonies of the said given category of bacteria. More particularly, the incubation medium comprises at least an antioxidant agent such as pyruvate or catalase.

More particularly, in one embodiment, the kit further comprises:
a said detectable molecule or said second molecule bearing a detectable substance, preferably a fluorochrome or luminescent molecule or an enzyme, and/or
a solid substrate bearing a said second molecule capable of specifically reacting or binding with said labeling molecule.

More particularly, in one embodiment, the kit of the present invention further comprises:
a said detectable molecule comprising a said second reactive group capable of reacting with said first reactive group, and
a solid medium allowing visualization of the bacteria after incubating with the said modified monosaccharide compound, said reactants and said detectable molecule.

More particularly again, the kit comprises:
a said modified monosaccharide compound substituted by a said first reactive group comprising an azido or alkyne group, and
a said second reactive group of the detectable molecule bearing an alkyne or, respectively, azido group, and
possibly, said reactants comprising a copper catalyst and a tristriazolyl ligand.

In a first particular embodiment, said labeling molecule can be a detectable molecule, namely a molecule consisting in or bearing a detectable substance, namely a substance capable to be detected such as a fluorochrome or luminescent substance or an enzyme such as peroxidase, said enzyme being more particularly detected after reacting with a co-reactant.

In a further particular embodiment, useful for isolating and/or concentrating living bacteria, the said labeling molecule can be bound to a solid substrate when carrying out step b).

In a further particular embodiment, said labeling molecule is a molecule which is a first ligand or first binding protein bearing a said second reactive group and in step c) said living bacteria coupled to said first ligand or first binding protein is detected and/or immobilized by contacting said first ligand or first binding protein with a second molecule which is a second ligand or second binding protein reacting or binding specifically to said first ligand or first binding protein.

Then, advantageously, said first or second ligand or binding protein can react or be bound to a third binding protein bearing a said detectable substance such as a fluorochrome or luminescent substance or an enzyme such as peroxidase, said third binding protein binding specifically to a said first and/or second ligand or binding protein. Detecting said detectable substance via a said second ligand or second binding protein or third binding protein enables to amplify the signal of the said detectable substance.

More particularly, the first ligand or first binding protein can be:
biotin, said second binding protein being then avidin or streptavidin and said third binding protein being an antibody raised against biotin, or
avidin or streptavidin, said second ligand binding protein being then biotin and said third binding protein being an antibody raised against avidin or streptavidin, or a first antibody, said second binding protein being then a second antibody specific to said first antibody and said third binding protein being a third antibody specific to said first antibody.

More particularly, said labeling molecule is a first ligand, preferably biotin, bearing a said second reactive group, and in step c) said living bacteria coupled to said first ligand are detected by reaction of said bacteria with an antibody specific to said first ligand, said antibody bearing a detectable substance, preferably a fluorochrome or luminescent molecule or an enzyme.

More particularly again, said labeling molecule is a first ligand, preferably biotin, bearing a said second reactive group, and in step c) said living bacteria coupled to said first binding protein is immobilized by reacting said first ligand with a solid substrate, preferably magnetic beads, coupled to a said second binding protein, preferably avidin or streptavidin, before detecting said living bacteria by bacterial DNA enzymatic amplification or by reaction of said bacteria with a third binding protein reacting or binding specifically to said first ligand or second binding protein, said third binding protein bearing a detectable substance, preferably a fluorochrome or luminescent molecule or an enzyme, said third binding protein being preferably an antibody specific to said first ligand or first binding protein.

In one embodiment, more particularly, the labeling molecule can be an enzyme bearing the second reactive group such as a horseradish peroxidase (HRP) or an urease enzyme.

Such embodiment wherein said living bacteria are immobilized on said solid substrate enables to concentrate the sample into said bacteria and to quantify said living bacteria by any known method including DNA enzymatic amplification such as PCR, especially Real Time PCR or a method involving immunological reaction with a labeled antibody such as an ELISA test.

Other characteristics and advantages of the present invention will be more apparent in the light of the following detailed description and examples of illustrative and non-limitative embodiments.

EXAMPLE 1: SYNTHESIS OF COMPOUND (IA): 4EKDO-$N_3$ (6)

In the synthesis the following reagents and conditions have been used: (i) TsCI, pyridine. (ii) pyridine, $Ac_2O$. (iii) sodium azide. DMF. (iv) $CH_3ONa$, $CH_3OH$. (v) oxaloacetic acid, NaOH, $H_2O$. (vi) Dowex® 50 ($H^+$). (viii) $NH_4OH$.

Thin layer chromatography was performed over Merck 60 $F_{254}$ with detection by UV, and/or by charring with sulphuric acid or $KMnO_4$ or phosphomolybdic acid solutions. Silica gel 60 40-63 µm was used for flash column chromatography.

NMR spectra were taken on Bruker Avance 300 or 500 MHz spectrometers, using the residual protonated solvent as internal standard. Chemical shifts δ are given in parts per million (ppm) and coupling constants are reported as Hertz (Hz). Splitting patterns are designated as singlet (s), doublet (d), triplet (t), doublet of doublet (dd), doublet of doublet of doublet (ddd). Splitting patterns that could not be interpreted or easily visualized are designated as multiplet (m).

Mass spectra were taken on a Thermo Scientific TSQ or on a Bruker micrOTOFq or on a Waters LCT Premier XE (ToF), with electrospray ionization in the positive (ESI+) mode of detection.

IR-FT spectra were recorded on a Perkin Elmer Spectrum 100 spectrometer. Characteristic absorptions are reported in $cm^{-1}$.

Compound (Ia or 6) was prepared as follows with a final purification of epimer (Ia or 6) from the mixture (Ia or 6)/(I-1 or 6').

The following scheme 1 shows the various compounds involved in the steps of the synthesis.

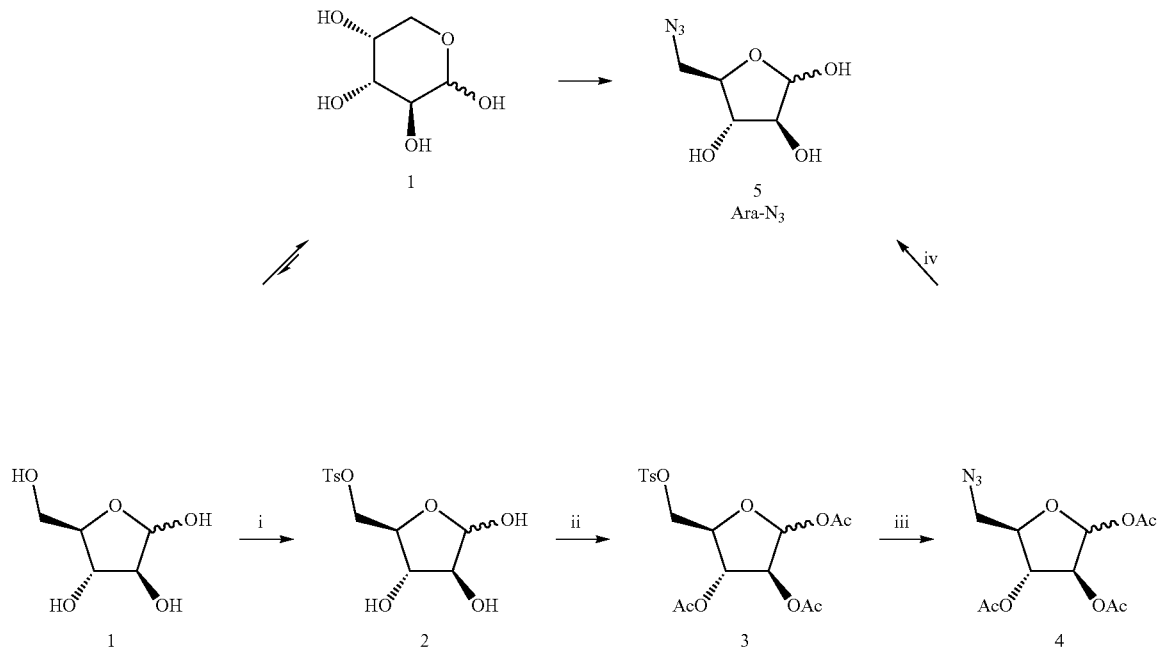

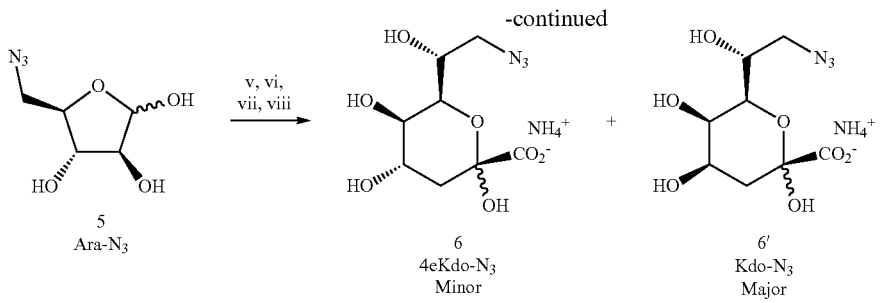

The reagents and conditions in the various steps are: (i) TsCl (1.1 eq.), pyridine (1.0 M), 100° C.->r. t., 18 h. (ii) pyridine/Ac$_2$O (2:1, 0.7 M), 18 h. (iii) NaN$_3$ (2.0 eq.), DMF (0.4 M), 80° C. 20 h, 15% over 3 steps, (iv) CH$_3$ONa (0.1 eq.). CH$_3$OH (0.2 M), r. t., 3 h, 99%. (v) Oxaloacetic acid (1.6 eq.), NaOH (pH 11), H$_2$O (0.5 M), r. t., 2 h. (vi) Dowex® 50 (H$^+$). (vii) 80° C., 20 min. (viii) NH$_4$OH. 1% of isolated 4eKdo-N$_3$ over 4 steps.

1) Preparation of 5-azido-5-deoxy-1,2,3-tri-O-acetyl-D-arabinofuranose (4)

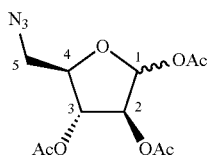 [SMILES: CC(=O)OC1O[C@H](CN=[N+]=[N-])[C@@H](OC(C)=O)[C@@H]1OC(C)=O]

Commercial D-arabinose (1) (6.00 g, 40 mmol) was heated at 100° C. for 2 hours in pyridine (40 mL). The solution was allowed to cool down, further treated with tosyl chloride (8.38 g, 44 mmol, 1.1 equiv.), and stirred for 16 hours at room temperature ((2), not isolated). Acetic anhydride (20 mL) was then added. After complete acetylation, as determined by TLC, solvents were evaporated, and residual traces were co-evaporated several times with toluene ((3), not isolated). The residue was dissolved in DMF (100 mL), sodium azide (5.20 g, 80 mmol, 2.0 eq.) was added, and the suspension was heated at 80° C. for 20 hours. After dilution with ethyl acetate and washing with water, the organic layer was dried over anhydrous magnesium sulfate and concentrated. The residue was purified by flash chromatography (petroleum ether/ethyl acetate 7:3). The first eluted product was determined to be the expected 5-azido-1,2,3-tri-O-acetyl-D-arabinofuranose (4) (1.83 g, 15%, α/β~2:1).

$^1$H-NMR (360 MHz, CDCl$_3$) δ (ppm): 6.41 (d, 0.33H, $J_{1,2}$ 3.5 Hz, H-1β); 6.23 (d, 0.67H, $J_{1,2}$~1 Hz, H-1α); 5.40-5.37 (m, 1.34H, H-2β, H-3β); 5.23 (d, 0.67H, $J_{1,2}$~1 Hz, H-2α); 5.06 (d, 0.67H, $J_{3,4}$ 4.6 Hz, H-3α); 4.30 (ddd, 0.67H, H-4α); 4.16-4.10 (m, 0.33H, H-4β): 3.69 (dd, 0.67H, $J_{5a,5b}$ 13.5, $J_{4,5a}$ 3.1 Hz, H-5aα); 3.61 (dd, 0.33H, $J_{5A,f5b}$13.1, $J_{4,5a}$ 3.6 Hz, H-5aβ); 3.51-3.43 (m, 1H, H-5bα, H-5bβ); 2.15, 2.13, 2.12, 2.11, 2.09 (6s, 18H, 6 CH$_3$CO).

$^{13}$C-NMR (62.5 MHz, CDCl$_3$) δ (ppm): 170.3, 170.0, 169.1 (3 C-0); 99.2 (C-1α); 93.5 (C-1β); 84.1 (C-4α); 80.8 (C-4β); 80.6 (C-3α); 77.4 (C-2α); 75.1 (C-2β); 74.8 (C-3β); 53.0 (C-5β); 51.3 (C-5α): 20.9, 20.6, 20.3 (3 CH$_3$).

LRMS (ESI+): [M+H]$^+$ 324.0.

HRMS (ESI+): [M+H]$^+$ (C$_{11}$H$_{15}$N$_3$NaO$_7$) Calc. m/z: 324.0802, found: 324.0802.

2) Preparation of 5-azido-5-deoxy-D-arabinofuranose (5)

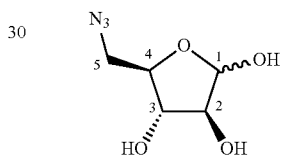

Protected 5-azido-1,2,3-tri-O-acetyl-D-arabinose (4) was then dissolved into anhydrous methanol (30 mL), treated with a methanolic solution of CH$_3$ONa (0.2 mol·L$^{-1}$, 3 mL) and stirred at room temperature for 3 hours under an argon atmosphere. After neutralization (Dowex® 50 (H$^+$)) filtration, and concentration, 5-azido-5-deoxy-D-arabinofuranose (5) was obtained in 99% yield (1.03 g).

Rf (dichloromethane/methanol 92:8): 0.28.

IR (cm$^{-1}$): 3367, 2106, 1281, 1040.

HRMS (ESI+): [M+H–N$_2$]$^+$ (C$_5$H$_{10}$NO$_4$) Calc. m/z: 148.0604. found: 148.0610.

Anomer alpha (5α):

$^1$H-NMR (500 MHz, D$_2$O) δ (ppm): 5.24 (d, 1H, $J_{1,2}$ 2.9 Hz. H-1); 4.17 (ddd, 1H, $J_{3,4}$ 6.4, $J_{4,5b}$, 5.8, $J_{4,5a}$ 3.5 Hz, H-4); 4.01 (dd, 1H, $J_{2,3}$ 4.6, $J_{1,2}$ 2.9 Hz, H-2); 3.97 (dd, 1H, $J_{3,4}$ 6.4, $J_{3,2}$ 4.6 Hz, H-3); 3.64 (dd, 1H, $J_{5a,5b}$ 13.6, $J_{4,5a}$ 3.5 Hz, H-5a); 3.44 (dd, 1H, $J_{5a,5b}$ 13.6, $J_{4,5b}$ 5.8 Hz, H-5b).

$^{13}$C-NMR (125 MHz, D$_2$O) δ (ppm): 101.0 (C-1); 81.3 (C-4); 81.2 (C-2); 76.3 (C-3); 51.5 (C-5).

Anomer beta (5β):

$^1$H-NMR (500 MHz, D$_2$O) δ (ppm): 5.28 (br d, 1H, $J_{1,2}$ 3.1 Hz, H-1); 4.10-4.05 (m, 2H, H-2, H-3); 3.89 (ddd, 1H, $J_{3,4}$ 7.1, $J_{4,5b}$ 6.5, $J_{4,5a}$ 3.5 Hz, H-4); 3.59 (dd, 1H, $J_{5a,5b}$ 13.3, $J_{4,5a}$ 3.5 Hz, H-5a); 3.42 (dd, 1H, $J_{5a,5b}$ 13.3, $J_{4,5b}$ 6.5 Hz, H-5b).

$^{13}$C-NMR (125 MHz, D$_2$O) δ (ppm): 95.2 (C-1); 79.6 (C-4); 75.8 (C-2); 74.7 (C-3); 52.6 (C-5).

3) Preparation of Ammonium 8-azido-3,8-dideoxy-D-gluco-octulosonate (4eKdo-N₃) (6)

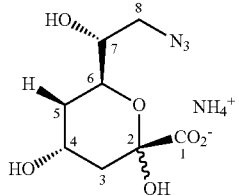

A cool (4° C.) solution of 5-azido-5-deoxy-D-arabino-furanose (5) (437 mg, 2.5 mmol) in water (2.1 mL) was added to a solution of oxaloacetic acid (528 mg, 4.0 mmol) in water (2.5 mL), the pH of which has been adjusted to ~11 by addition of aqueous NaOH (10M). After being stirred for two hours at room temperature, the solution was neutralized (Dowex® 50 (H⁺)), filtrated, and heated 20 min at 80° C. After its pH had been adjusted to ~7 with AcOH (0.5M), the resulting Kdo-N₃/4eKdo-N₃ mixture was purified by anion exchange chromatography (Dowex® 1X8 (HC0₂⁻)). Initial elution with water gave unreacted (5) (150 mg, 34%). Further elution with a concentration gradient of formic acid (0.5 mol·L⁻¹ to 2.0 mol·L⁻¹), freeze-drying, treatment with a Dowex® 50 (H) resin, and neutralization by ammonia (0.2 mol·L⁻¹), gave after concentration, a mixture of Kdo-N. and 4eKdo-N₃. This mixture of (6) (1a) and (6') (I-1) was again purified by anion exchange chromatography (Dowex® 1X8 (HC0₂⁻)) by elution with a slow concentration gradient of formic acid (1.5 mol·L⁻¹ to 2.0 mol·L⁻¹), freeze-drying, treatment with a Dowex® 50 (H⁺) resin, and neutralization by ammonia (0.2 mol·L⁻¹), gave after concentration, the ammonium of the specific minor epimer 8-azido-3,8-dideoxy-D-gluco-octulosonate (6 or Ia), 7 mg.

Rf (ethyl acetate/ethanol/water 65:30:5): 0.22.
Rf (isopropyl alcohol/water 9:1): 0.38.
IR (cm⁻¹): 3296, 2931, 2104 (N₃), 1612, 1384, 1283, 1072, 805.
LRMS (ESI): 262.1.
HRMS (ESI): [M–H]" ($C_8H_{12}N_3O_7$) Calc. m/z: 262.0681, found: 262.0669.

Major conformer pyranose form (NMR 7.5):
¹H-NMR (600 MHz, D₂O) δ: 4.15 (dd, 1H, $J_{6,7}$ 9.1, $J_{5,6}$ 1.0 Hz, H-6); 4.10 (ddd, 1H, $J_{4,5}$ 4.1. $J_{4,3a}$ 3.7, $J_{4,3b}$ 2.6 Hz, H-4); 4.03 (ddd, 1H, $J_{6,7}$ 9.1, $J_{7,8a}$ 6.3, $J_{7,8a}$ 2.8 Hz, H-7); 3.82 (dd, 1H, $J_{4,5}$ 4.1, $J_{5,6}$ 1.0 Hz, H-5); 3.63 (dd, 1H, $J_{8a,8b}$ 13.1, $J_{7,8a}$ 2.8 Hz, H-8a); 3.47 (dd, 1H, $J_{8a,8b}$ 13.1, $J_{7,8b}$ 6.3 Hz, H-8b); 2.23 (dd, 1H, $J_{3a,3b}$ 15.0, $J_{4,3a}$ 3.7 Hz, H-3a); 1.84 (dd, 1H, $J_{3a,3b}$ 15.0, $J_{4,3b}$ 2.6 Hz, H-3b).
¹³C-NMR (150 MHz, D₂O) δ: 177.9 (C-1); 97.1 (C-2); 69.3 (C-7); 68.6 (C-6); 68.5 (C-4) 66.8 (C-5); 54.7 (C-8); 32.7 (C-3).

Major conformer furanose form (NMR 3.0):
¹H-NMR (600 MHz, D₂O) δ: 4.61 (ddd, 1H, $J_{4,5}$ 6.0, $J_{4,3a}$ 5.0, $J_{4,5}$ 4.8 Hz, H-4); 4.37 (dd, 1H, $J_{4,5}$ 4.8, $J_{5,6}$ 3.5 Hz, H-5); 3.91 (dd, 1H, $J_{6,7}$ 8.2, $J_{5,6}$ 3.5 Hz, H-6); 3.90 (ddd, 1H, $J_{6,7}$ 8.2, $J_{7,8b}$ 6.7, $J_{7,8a}$ 2.6 Hz, H-7); 3.59 (dd, 1H, $J_{8a,8b}$ 13.0, $J_{7,8b}$ 2.6 Hz, H-8a); 3.51 (dd, 1H, $J_{8a,8b}$ 13.0, $J_{7,8b}$ 6.7 Hz, H-8b); 2.40 (dd, 1H, $J_{3a,3b}$ 13.9, $J_{4,3a}$ 5.0 Hz, H-3a); 2.37 (dd, 1H, $J_{3a,3b}$ 13.9, $J_{4,3b}$ 6.0 Hz, H-3b).
¹³C-NMR (150 MHz, D₂O) δ: 178.4 (C-1); 103.8 (C-2); 82.0 (C-5); 72.7 (C-4); 71.8, 71.6 (C-6, C-7); 54.1 (C-8); 45.6 (C-3).

Minor conformer pyranose form (NMR 1.5):
¹H-NMR (600 MHz, D₂O) δ: 4.01 (ddd, Hz. H-4); 3.96 (ddd, 1H, $J_{6,7}$ 8.9. $J_{7,8b}$ 6.2, $J_{7,8a}$ 2.7 Hz, H-7); 3.91 (dd, 1H, $J_{6,7}$ 8.9, $J_{5,6}$ 1.2 Hz, H-6); 3.76 (dd, 1H, $J_{4,5}$ 4.2, $J_{5,6}$ 1.2 Hz, H-5); 3.62 (dd, 1H, $J_{8a,8b}$ 13.2, $J_{7,8a}$ 2.7 Hz, H-8a); 3.45 (dd, 1H, $J_{8a,8b}$ 13.2, $J_{7,8b}$ 6.2 Hz, H-8b); 2.16 (dd, 1H, $J_{3a,3b}$ 15.1, $J_{4,3a}$ 4.0 Hz. H-3a); 2.12 (dd, 1H, $J_{3a,3b}$ 15.1, $J_{4,3b}$ 3.1 Hz, H-3b).
¹³C-NMR (150 MHz, D₂O) δ: 176.7 (C-1); 96.8 (C-2); 69.4 (C-7); 70.9 (C-6); 68.5 (C-4); 66.9 (C-5); 54.8 (C-8); 34.2 (C-3).

Minor conformer furanose form (NMR 1.0):
¹H-NMR (600 MHz, D₂O) δ: 4.58 (ddd, 1H, $J_{4,3a}$ 5.6, $J_{4,5}$ 4.1, $J_{4,3b}$ 1.7 Hz, H-4); 4.24 (dd, 1H, $J_{5,6}$ 4.5, $J_{4,5}$ 4.1 Hz, H-5); 3.97 (dd, 1H, $J_{6,7}$ 7.5, $J_{5,6}$ 4.5 Hz, H-6); 3.91 (dd, 1H, $J_{6,7}$ 7.5, $J_{7,8b}$ 6.6, $J_{7,8a}$ 3.1 Hz, H-7); 3.60 (dd, 1H, $J_{8a,8b}$ 13.2, $J_{7,8a}$ 3.1 Hz, H-8a); 3.51 (dd, 1H, $J_{8a,8b}$ 13.2, $J_{7,8b}$ 6.6 Hz, H-8b); 2.55 (dd, 1H, $J_{3a,3b}$ 14.3, $J_{4,3a}$ 5.6 Hz, H-3a); 2.15 (dd, 1H, $J_{3a,3b}$ 14.3, $J_{4,3b}$ 1.7 Hz, H-3b).
¹³C-NMR (150 MHz, D₂O) δ: 178.3 (C-1); 104.3 (C-2); 83.7 (C-5); 73.0 (C-4); 71.9 (C-6); 70.9 (C-7); 54.5 (C-8); 45.6 (C-3).

EXAMPLE 2

Comparison of labeling of living bacteria with compounds 4eKdo-N₃(Ia) of the present invention and compound Kdo-N₃ (I-1).

1) Material and Methods.

1.1) Bacterial Strains and Growth Conditions.

The 28 bacterial strains listed in Table 1 are grown in the culture media and conditions listed in tables 1 and 2. All strains were grown in a rotary shaker (160 rpm) at 30 or 37° C.

TABLE 1

| microorganisms BACTERIA | REFERENCES | Growth conditions |
|---|---|---|
| *Bacillus cereus* | Laboratory strain (FIEROBE team LCB/CNRS) | TSB-24 H-37° C. |
| *Bacillus cereus* | CIP 66.24T | TSB-24 H-37° C. |
| *Bacillus cereus paris* | Laboratory strain (HENRY team/CNRS) | TSB-24 H-30° C. |
| *Enterococcus durans* | Laboratory strain (FIEROBE team LCB/CNRS) | TSB-24 H-37° C. |
| *Enterococcus faecalis* | Laboratory strain (FIEROBE team LCB/CNRS) | TSB-24 H-37° C. |
| *Escherichia coli* K12 | MG1655 | LB-24 H-37° C. |
| *Escherichia coli* O86 | Laboratory strain (DENAMUR team/INSERM) | LB-24 H-37° C. |
| *Stenotrophomonas maltophilia* | Clinical strain (LASCOLA/Marseille, La Timone) | TSB-24 H-37° C. |
| *Streptococcus agalactiae* | Clinical strain (LASCOLA/Marseille, La Timone) | TSB-24 H-37° C. |
| *Vibrio cholerae* | CIP 104151 | TSB-24 H-37° C. |
| *Klebsiella pnuemoniae* | CIP 101114 | TSB + 5% sheep blood-24 H-30° C. |
| *Klebsiella pnuemoniae* | Clinical strain (LASCOLA/ Marsellie, La Timone) | TSB-24 H-37° C. |
| *Legionella pneumophila* sg6 | LG 0846 3022 (CNRL, environmental strain) | YEC + sup. *Legionella* 10%-24 H-37° C. |
| *Listerla monocytogenes* 1/2 | CIP 82.110T | BHI-24 H-37° C. |
| *Listerla monocytogenes* 1/2a | CIP 100607 | BHI-24 H-37° C. |

TABLE 1-continued

| microorganisms BACTERIA | REFERENCES | Growth conditions |
|---|---|---|
| *Micrococcus luteus* | Laboratory strain (FIEROBE team LCB/CNRS) | TSB-24 H-30° C. |
| *Neisseria gonorrhoeae* | CIP 79.16T | TSB + 10% Horse blood-24 H-37° C. |
| *Neisseria meningitidis* | CIP 107858 | TSB + 10% Horse blood-24 H-37° C. |
| *Proteus mirabilis* | Clinical strain (LASCOLA/ Marseille, La Timone) | TSB-24 H-37° C. |
| *Providencia stuartii* | Clinical strain (LASCOLA/ Marseille, La Timone) | TSB-24 H-37° C. |
| *Pseudomonas fluorescens* Migula | ATOC 4927 | TSB-24 H-37° C. |
| *Pseudomonas fluorescens* Paris | Laboratory strain (HENRY team/CNRS) | TSB-24 H-37° C. |
| *Salmonella typhimurium* 12023 | Laboratory strain (BARRAS team/CNRS) | TSB-24 H-37° C. |
| *Serratia marcescens* | CIP102446 | TSB-24 H-30° C. |
| *Serratia marcescens* | Clinical strain (LASCOLA/ Marseille, La Timone) | TSB-24 H-37° C. |
| *Staphyloccus aureus* | Clinical strain (LASCOLA/ Marseille, La Timone) | TSB-24 H-37° C. |
| *Staphyloccus aureus aureus* | CIP 53-156 | TSB-24 H-37° C. |
| *Staphyloccus epidermis* | Laboratory strain (FIEROBE team LCB/CNRS) | TSB-24 H-37° C. |
| *Staphylococcus saprophyticus* | Clinical strain (LASCOLA/ Marseille, La Timone) | TSB-24 H-37° C. |
| *Stenotrophomonas maltophilia* | Clinical strain (LASCOLA/ Marseille, La Timone) | TSB-24 H-37° C. |
| *Streptococcus agalactiae* | Clinical strain (LASCOLA/ Marseille, La Timone) | TSB-24 H-37° C. |
| *Vibrio cholerae* | CIP 104151 | TSB-24 H-37° C. |

TABLE 2

| | Composition | Provider | Reference |
|---|---|---|---|
| Tryptic Soy Broth (TSB) | casein peptone (pancreatic) 17 g/l + Soya peptone (papain digest.) 3 g/l + Sodium chloride 5 g/l + Dipotassium hydrogen phosphate 2.5 g/l + Glucose 2.5 g/l pH 7.3 | Sigma Aldrich (USA) | 22092 |
| Brain Heart Infusion (BHI) | brain infusion solids 12.5 g/l + beef heart infusion solids 5 g/l + proteose peptone 10 g/l + glucose 2 g/l + sodium chloride 5 g/l + di sodium phosphate 2.5 g/l | Oxoid (GB) | CM1135 |
| YEC | yeast extract 10 g/l + Casamino acid | Becton Dickinson (USA) | Bacto 212720 |
| Luria Bertani (LB) | Bactotryptone 10 g/l+ | Becton Dickinson (USA) | 211699 |
| | Bacto yeast extract 5 g/l+ | Becton Dickinson (USA) | 212720 |
| | Sodium chloride+ | Sigma Aldrich (USA) | 55886 |
| | pastagar 15 g/l pH 7.2 | Biorad (USA) | 64946 |

1.2) Copper Catalyzed Click Chemistry

Overnight cultures were diluted 100 times in fresh medium (final volume 100 µl) containing Kdo-N$_3$ (1-1) or 4eKdo-N$_3$ (Ia) (10 mM). Bacteria were incubated at 30 or 37° C. for 24 hours and then washed 3 times with phosphate buffer (0.05 M, pH 7.5) by centrifugation at 13.000×g for 2 min at room temperature.

Two fluorochrome-alkyne probes of following formula A488-yne (7a) and A594-yne (7b) were used:

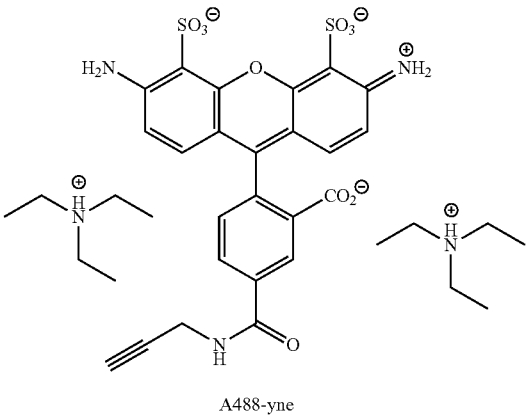

A488-yne

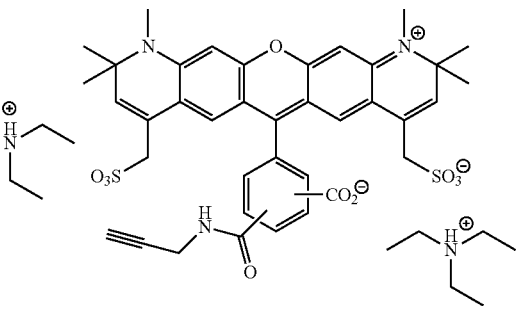

A594-yne

CuSO$_4$ and TGTA, at a final concentration of 2 mM and 4 mM respectively, were mixed overnight in phosphate buffer (0.05 M, pH 7.5) at 37° C. under vigorous shaking. Next, aminoguanidine, sodium ascorbate and fluorochrome-alkyne (7a) or (7b) at a final concentration of 4 mM, 5 mM and 1 mM respectively were added to CuSO$_4$/TGTA overnight mix. Finally, bacteria were resuspended in this solution and incubated for 30 minutes at 37° C. Cells were then washed 3 times with phosphate buffer by centrifugation at 13,000×g for 2 min at room temperature and analyzed by microscopy.

1.3) Fluorescence Microscopy.

Bacteria were inoculated onto glass cover slips and covered with a thin (1 mm of thickness) semisolid 1% agar pad made with dilute LB (1/10 in phosphate buffer (0.05 M, pH 7.5)). Images were recorded with epifluorescence automated microscope (Nikon TE2000-E-PFS, Nikon, France) equipped with a CoolSNAP HQ 2 camera (Roper Scientific, Roper Scientific SARL, France) and a 100×/1.4 DLL objective. Excitation light was emitted by a 120 W metal halide light and signal was monitored using appropriate filters. Digital analysis and image processing were conducted by a custom automation script (Visual Basic) under Metamorph 7.5 (Molecular Devices, Molecular Devices France, France).

2) Results

21.) 28 different strains of bacteria have been tested with both compounds 4eKdo-N$_3$ (Ia) and Kdo-N$_3$ (I-1) in comparison.

These strains were grown first in the presence of compound (Ia) or (I-1) and the incorporation of the azido chemical reporter into the bacteria was monitored in a subsequent step, using copper-catalysed azide-alkyne cycloaddition in the conditions previously described, with copper sulfate, sodium ascorbate, TGTA, a water-soluble tris(triazolyl) ligand for copper (I), and a fluorochrome-alkyne probe of above formula (7a) or (7b), for 30 minutes as above disclosed.

In these experiments, strains showing highly distinctive fluorescence on their membrane, indicative of an effective metabolic incorporation of the chemical reporter have been marked "+" in the table 3 below, the absence of labeling has been marked "−" in table 3, and the not tested bacteria have been marked "NT" in table 3.

Table 3:

TABLE 3

| Strain | Kdo-N$_3$ | 4eKdo-N$_3$ |
|---|---|---|
| *Bacillus cereus* | NT | + |
| *Bacillus cereus* | NT | + |
| *Bacillus cereus* paris | NT | + |
| *Enterococcus durans* | NT | + |
| *Enterococcus faecalis* | − | + |
| *Escherichia coli* K12 | + | + |
| *Escherichia coli* O86 | + | + |
| *Klebsiella pneumoniae* | + | + |
| *Klebsiella pneumoniae* | + | + |
| *Legionella pneumophila* sg6 | + | + |
| *Listeria monocytogenes* ½ | − | + |
| *Listeria monocytogenes* ½a | − | + |
| *Micrococcus luteus* | − | + |
| *Neisseria gonorrhoeae* | − | + |
| *Neisseria meningitidis* | + | + |
| *Proteus mirabilis* | + | + |
| *Providenda stuartii* | + | + |
| *Pseudomonas fluorescens* Migula | + | + |
| *Salmonella Typhimurium* 12023 | + | + |
| *Serratia marcescens* | + | + |
| *Serratia marcescens* | + | + |
| *Staphylococcus aureus* | − | + |
| *Staphylococcus aureus aureus* | − | + |
| *Staphylococcus epidermis* | − | + |
| *Staphylococcus saprophyticus* | NT | + |
| *Stenotrophomonas maltophilia* | + | + |
| *Streptococcus agalactiae* | NT | + |
| *Vibrio cholerae* | + | + |

These experiments shows that compound (Ia) of the present invention is assimilated by a broad range of bacteria and interestingly, compound (Ia) is assimilated by the following Gram positive bacteria which did not assimilate compound (I-1): *Enterococcus faecalis*. *Listeria monocytogenes, Micrococcus luteus, Staphylococcus aureus, Staphylococcus aureus aureus* and *Staphylococcus epidermis* as well as the Gram negative *Neisseria gonorrhoeae*.

The invention claimed is:

1. A method for labeling specifically living bacteria in a sample comprising bacteria, wherein the method comprises the steps of:
   a) incubating said bacteria of said sample with at least one modified monosaccharide compound comprising a first reactive group Ra, which is capable to chemically react with a second reactive group, so that a residue bearing said first reactive group is incorporated into the envelope of said living bacteria, and
   b) contacting said residue incorporated into the envelope of said living bacteria with a labeling molecule comprising said second reactive group, for generating the chemical reaction of said first reactive group of said residue incorporated within said living bacteria with said second reactive group of said labeling molecule, resulting in a covalent link, wherein said residue is not an endogenous ulosonic acid residue of the envelope of said bacteria, said modified monosaccharide compound having the following formula (I), or a salt thereof:

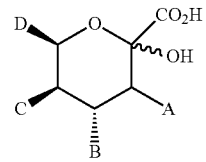

wherein

A is H, OH, or NH$_2$, wherein OH and NH$_2$ being substituted or not by a protecting group selected from the group consisting of alkyl, hydroxyalkyl, acyl, formyl and imidoyl groups, B is OH or NH$_2$, wherein OH and NH$_2$ being substituted or not by a protecting group selected from the group consisting of alkyl, hydroxyalkyl, acyl, formyl and imidoyl groups and C is OH or NH$_2$, OH and NH$_2$ being substituted or not by a protecting group selected in the group consisting of alkyl, hydroxyalkyl, acyl, formyl and imidoyl groups, and D is a $C_2$ or $C_4$ alkyl, each carbon being substituted or not by OH or NH$_2$, wherein the OH and NH$_2$ are each substituted or not by a protecting group selected from the group consisting of alkyl, hydroxyalkyl, acyl, formyl and imidoyl groups, and the D group is substituted by said first reactive group, wherein the first reactive group Ra is selected from the group consisting of -N$_3$, a group bearing an azido, an alkyne, and a group bearing an alkyne, and said second reactive group is selected from the group consisting of -N$_3$, a group bearing an azido, an alkyne, and a group bearing an alkyne, wherein said first reactive group is capable of reacting with said second reactive group via an azide alkyne cycloaddition.

2. The method according to claim 1, wherein said modified monosaccharide is a compound of formula (I) wherein D=-CHOH—CH$_2$—OH, A=H, B=OH, C=OH, wherein the OH of B, C and D is substituted or not by a protecting group and at least one OH of D group is substituted by said first reactive group Ra.

3. The method according to claim 1, wherein said modified monosaccharide compound is a compound of formula (I) wherein D=-CHOH—CH$_2$—Ra, A=H, B=OH, C=OH, wherein the OH of B, C and D is substituted or not by a protecting group.

4. The method according to claim 1, wherein Ra is —N$_3$ or —C≡CH.

5. The method according to claim 1, wherein said modified monosaccharide compound is a compound having the following stereoisomer formula (Ia), or a salt thereof:

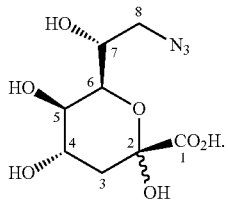

6. The method according to claim 1, wherein said bacteria are Gram positive bacteria.

7. The method according to claim 1, for labeling one or more species bacteria selected from the group consisting of *Bacillus cereus, Bacillus cereus paris, Enterococcus durans, Enterococcus faecalis, Escherichia coli, Klebsiella pneumonia, Legionella pneumophila, Listeria monocytogenes, Micrococcus luteus, Neisseria gonorrhoeae, Neisseria meningitides, Proteus mirabilis, Providencia stuartii, Pseudomonas fluorescens Migula, Salmonella typhimurium, Serratia marcescens, Staphylococcus aureus, Staphylococcus aureus aureus, Staphylococcus epidermis, Staphylococcus saprophyticus, Stenotrophomonas maltophilia, Streptococcus agalactiae* and *Vibrio cholerae*.

8. The method according to claim 1, wherein said method comprises the further step of:
   c) detecting living bacteria which comprises detecting whether said bacteria comprise said labeling molecule bound to their envelope and/or immobilizing said living bacteria bearing said labeling molecule onto a solid substrate, wherein said labeling molecule is a molecule comprising a detectable substance or capable to react or to be bound to a detectable substance or said labeling molecule is a first molecule bearing said second reactive group, said first molecule being capable to react or to be bound to a second molecule and/or to a solid substrate, said second molecule comprising a detectable substance and/or said second molecule being bound or capable to be bound to said solid substrate.

9. The method according to claim 8 for specifically detecting living bacteria of said bacteria in a sample comprising bacteria, wherein said labeling molecule is a detectable molecule comprising a detectable substance, wherein in the step c), detecting living bacteria comprises detecting whether said bacteria comprise said detectable molecule bound to the glycans of their outer membrane.

10. The method according to claim 8, wherein said labeling molecule is a first ligand or first binding protein bearing said second reactive group and in step c) said living bacteria coupled to said first ligand or first binding protein is detected and/or immobilized by contacting said first ligand or first binding protein with a second ligand or second binding protein reacting or binding specifically to said first ligand or first binding protein.

11. The method according to claim 8, wherein said labeling molecule is a first ligand, bearing said second reactive group, and in step c) said living bacteria coupled to said first ligand are detected by reaction of said bacteria with an antibody specific to said first ligand, said antibody bearing a detectable substance.

12. A kit for carrying out the method of claim 1, which comprises:
   said modified monosaccharide compound of formula (I), and
   said labeling molecule comprising said second reactive group capable of reacting with said first reactive group, and optionally
   reactants for generating the reaction of said first reactive group with said second reactive group of said labeling molecule.

13. The kit according to claim 12, which further comprises:
   a detectable molecule or second molecule bearing a detectable substance comprising a fluorochrome or luminescent molecule or an enzyme, and/or
   a solid substrate bearing said second molecule capable of specifically reacting or binding with said labeling molecule, and optionally
   a culture or incubation medium allowing the growth of said bacteria.

14. The method according to claim 1, wherein said residue is a not naturally occurring stereoisomer of an endogenous ulosonic acid residue of the envelope of said bacteria.

15. The method according to claim 1, wherein the protecting group is an alkyl, hydroxyalkyl, acyl, or formyl group.

16. The method according to claim 2, wherein the protecting group is an alkyl, hydroxyalkyl, acyl, or formyl group.

17. The method according to claim 1, wherein the first reactive group is —$N_3$ or a group bearing an azido, and the second reactive group is an alkyne or a group bearing an alkyne.

18. The method according to claim 11, wherein the detectable substance is a fluorochrome or luminescent molecule or an enzyme.

19. The method according to claim 11, wherein the first ligand is biotin.

20. The method according to claim 1, for labeling one or more bacteria selected from the group consisting of *Neisseria gonorrhoeae, Enterococcus faecalis, Listeria monocytogenes, Micrococcus luteus, Staphylococcus aureus, Staphylococcus aureus aureus,* and *Staphylococcus epidermis*.

* * * * *

UNITED STATES PATENT AND TRADEMARK OFFICE
CERTIFICATE OF CORRECTION

PATENT NO. : 11,199,542 B2
APPLICATION NO. : 15/570416
DATED : December 14, 2021
INVENTOR(S) : Dukan et al.

It is certified that error appears in the above-identified patent and that said Letters Patent is hereby corrected as shown below:

In the Specification

• Column 1, Line 13, "hearing" change to --bearing--

• Column 5, Lines 40-50, formula " 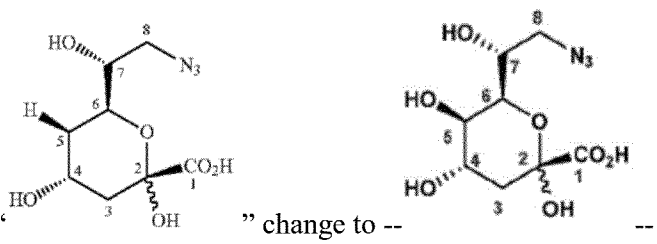 " change to -- --

• Column 6, Lines 5-15, formula " 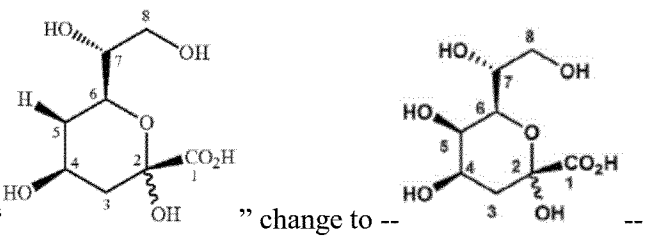 " change to -- --

• Column 6, Lines 15-25, formula " 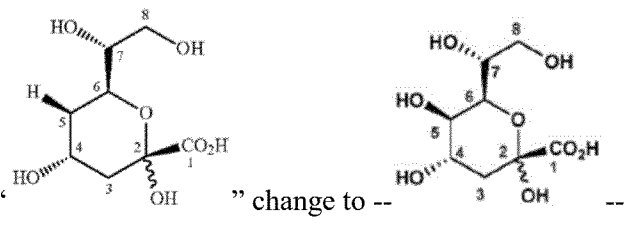 " change to -- --

• Column 6, Line 67, "*mahlophilia*" change to --*maltophilia*--

• Column 7, Line 21, "cell/mi" change to --cell/ml--

Signed and Sealed this
Sixth Day of September, 2022

Katherine Kelly Vidal
*Director of the United States Patent and Trademark Office*

- Column 12, Line 15, "KMn04" change to --KMnO$_4$--
- Column 15, Lines 5-15, formula " 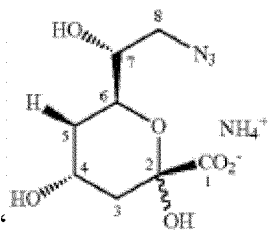 " change to -- 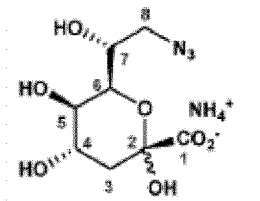 --
- Column 15, Line 25, "(HC0$_2$-''))" change to --(HCO$_2^-$))--
- Column 15, Line 44, "(C$_8$H$_{12}$N$_3$0$_7$)" change to --(C$_8$H$_{12}$N$_3$O$_7$)--
- Column 18, Lines 20-35, formula " 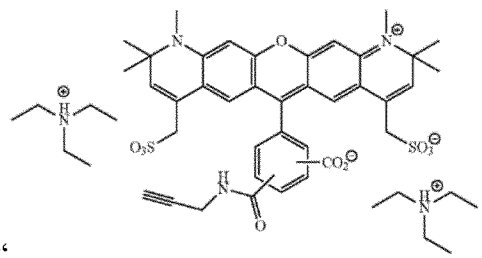 " change to -- 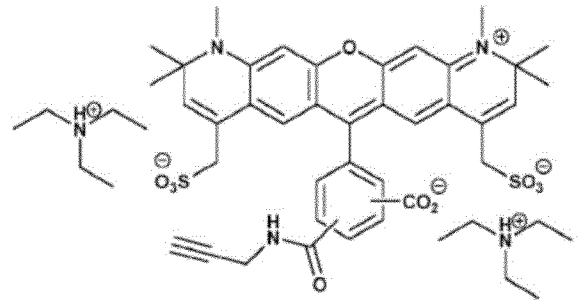 --